United States Patent [19]

Mathis et al.

[11] Patent Number: 5,512,493
[45] Date of Patent: Apr. 30, 1996

[54] METHOD OF AMPLIFYING THE EMISSION SIGNAL OF A LUMINESCENT COMPOUND

[75] Inventors: Gérard Mathis, Bagnols-sur-Ceze; Christophe Dumont, Connaux; Daniel Aspe, Laudun; Muriel Foyentin, Avignon; Etienne J. Jolu, Bagnols-sur-Ceze; Dominique Nuti, Avignon, all of France

[73] Assignee: CIS Bio International, France

[21] Appl. No.: 68,843

[22] Filed: May 26, 1993

Related U.S. Application Data

[63] Continuation of Ser. No. 729,228, Jul. 12, 1991, abandoned.

[30] Foreign Application Priority Data

Jul. 13, 1990 [FR] France .................... 90 08981

[51] Int. Cl.⁶ .................... G01N 33/542; G01N 33/533
[52] U.S. Cl. .................... 436/537; 436/536; 436/546; 436/81; 436/164; 436/172; 435/7.1
[58] Field of Search .................... 435/7.1, 968; 436/536, 436/537, 546, 81, 82, 164, 800, 805, 172

[56] References Cited

U.S. PATENT DOCUMENTS

| | | |
|---|---|---|
| 4,542,104 | 9/1985 Stryer et al. | 436/536 |
| 4,822,733 | 4/1989 Morrison | 435/6 |
| 4,927,923 | 5/1990 Mathis et al. | 540/456 |

OTHER PUBLICATIONS

I. Hemmilla, Clin. Chem. 31/3, 359–370 (1985).
Soini et al, CRC Critical Reviews in Analytical Chemistry, vol. 18 No. 2 pp. 105–154 (1987) "Time–Resolved Fluorescence of Lanthanide Probes and Applications in Biotechnology".
Morrison Analytical Biochemistry 174 101–120 (1984).

*Primary Examiner*—Toni R. Scheiner
*Assistant Examiner*—Lora M. Green
*Attorney, Agent, or Firm*—Marshall & Melhorn

[57] ABSTRACT

The invention relates to a method of amplifying the emission signal of a luminescent compound in a luminescent assay, and to its use in a luminescent method of detecting and/or determining an analyte in a medium in which it may be present.

15 Claims, No Drawings

METHOD OF AMPLIFYING THE EMISSION SIGNAL OF A LUMINESCENT COMPOUND

This application is a continuation of application Ser. No. 07/729,228, filed Jul. 12, 1991, abandoned.

The invention relates to a method of amplifying the emission signal of a luminescent compound.

It further relates to a luminescent method of detecting and/or determining an analyte in a medium in which it is present, using this method of amplifying the emission signal of a luminescent compound.

Immunoassays are widely used at the present time for the qualitative and quantitative analysis of compounds in biological fluids.

Of the techniques which exist, fluorimetric assays have become increasingly important.

In fact, they have a number of advantages which include sensitivity, speed of measurement, stability and safety of reagents labeled with fluorescent compounds, and relatively low cost.

It is known that methods of detection which utilize fluorescence are intrinsically very sensitive and may allow lower detection limits that those achieved by immunoassays employing radiolabeled reagents, in particular by the use of laser modulated light sources (I. Wieder, Immunofluorescence and related staining techniques, 1978, Elsevier).

However, the sensitivity of the technique depends on numerous parameters.

It is apparent from the prior art that the fluorescent molecule chosen as the tracer must possess the following properties:

it must contain a chemical functional group which permits coupling with the biological molecule without denaturing it or modifying its immunological properties;

the molar absorption coefficient of the fluorescent molecule must be as high as possible;

the quantum yield of fluorescence must be as high as possible;

the Stokes shift must be as large as possible;

the emission wavelength must be greater than 500 nm if possible;

the fluorescent molecule must be soluble in water or buffer solutions.

These conditions are detailed for example in the article by E. SOINI et al., Clin. Chem. 25, 353 (1979), or in I. HEMMILLA, Clin. Chem. 31/3, 359 (1985).

In the field of fluorescent immunoassays, and in particular homogeneous immunoassays, one of the conditions necessary for obtaining a high sensitivity assay is to use a fluorescent marker which possesses a high quantum yield and is stable at low dilution in the measuring medium.

"Homogeneous immunoassay" is understood as meaning an assay in which the signal of the tracer molecule is modified when the ligand binds to the receptor or when 2 ligands bind to the receptor (one or other being the molecule which it is desired to assay), avoiding the need to separate the labeled molecules which remain free in the measuring medium from those which are bound, before the measurement is carried out.

In the case of homogeneous fluorescent immunoassays utilizing energy transfer, the condition of high quantum yield of the donor is all the more important since it also determines the transfer efficiency and consequently the quantity of light emitted by the acceptor, which is measured (Ullman et al., Clinical Lab. Techniques for the 1980's, 1980, 13–43, edited by A. R. Liss).

These criteria for selection of the luminescent tracer apply similarly to assays utilizing phosphorescent molecules.

The sensitivity of the measurement is also greatly affected by the "background" consisting of the emission of the other molecules present in the test sample which are capable of being excited at the same time as the luminescent tracer and of emitting at the measurement wavelength.

This problem is particularly acute in the case of assays in a serum medium in which numerous molecules (proteins etc.) are liable to interfere with the measurement.

In the case of fluorescent immunoassays, the time-resolved methods of measuring fluorescence make it possible to mitigate this disadvantage to some extent. The principle of these methods is to measure the fluorescence emitted by a tracer molecule with a relatively long emission lifetime, the measurement being time-delayed beyond the emission lifetime of the other molecules present.

It is necessary in this case to use fluorescent tracer molecules with a relatively long lifetime, such as rare earth chelates.

This technique can be used particularly in the case of homogeneous fluorescent immunoassays utilizing energy transfer.

U.S. Pat. No. 4,822,733 describes a homogeneous method of detecting an analyte in a sample using a receptor and an analyte which are labeled with fluorescent molecules having different lifetimes. Measurement of the fluorescence resulting from energy transfer is carried out at a time beyond the emission lifetime of the molecule with the shortest lifetime.

Nevertheless, time-resolved fluorescence measurement alone is not capable of solving one of the important problems posed by homogeneous fluorescent immunoassays utilizing energy transfer, namely the existence of a residual signal of the tracer carrying the fluorescent donor molecule during measurement at the fluorescence wavelength of the acceptor (Morrison, Anal. Biochem. 174, 119, 1988). This phenomenon is even more important when the procedure involves large excesses of tracer, as in the case of sandwich techniques, or when a competitive procedure is used and the labeled antigen is not pure.

This important problem which limits the sensitivity has been referred to by Ullman et al. (Clinical Lab. Techniques for the 1980's, 1980, 13–43, edited by A. R. Liss), who proposes the use of an anti-tracer antibody to inhibit the free tracer in solution.

This phenomenon is further aggravated if the lifetime of the donor is long compared with that measured on the acceptor.

Unexpectedly, it has now been found that by using, as the luminescent donor compound, molecules which have a low overall quantum yield and which, according to the prior art, are therefore unsuitable for use in an assay, especially a luminescent immunoassay, it is possible in particular to solve the problem of the residual signal of the fluorescent tracer without detracting from the transfer efficiency, and consequently to enhance the sensitivity of the assay.

In fact, it has been observed that by using acceptor compounds at concentrations comparable to those indicated in the literature for use with a donor compound having a high quantum yield, it is possible to obtain a high transfer efficiency with a donor compound having a low overall quantum yield, and it has been found that the intensity of the signal measured on the acceptor is greater than that of the signal measured on the donor compound alone. This observation makes it possible to carry out a precise and sensitive measurement with a donor compound having a low overall quantum yield, which is surprising in the light of the prior art.

The method in question is therefore a method of amplifying the emission signal of a luminescent donor compound. Advantageously, this amplification will be all the more significant, the lower the overall quantum yield of the luminescent donor compound.

One of the hypotheses by which the mechanism of this phenomenon can be explained is that the high transfer efficiency observed when using a luminescent donor compound having a low overall quantum yield is related only to the yield of radiative deactivation of the emission level of the donor and not to its overall quantum yield, as taught in the prior art.

In the case of the rare earth chelates and cryptates used as fluorescent tracers, the photophysical mechanisms between the absorption and emission of light within the rare earths can be represented in the following manner, as indicated for example by N. Sabbatini et al. in Supramolecular Biochemistry, 1987, p. 187–206, Reidel Dordrecht, edited by V. Balzani:

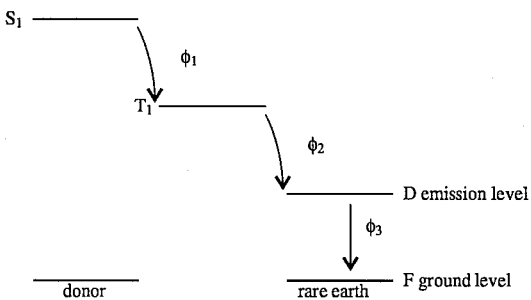

The excitation energy serves to populate the $S_1$ level, which populates the triplet by intersystem transition. The triplet transfers its energy to the emission level of the rare earth, which undergoes radiative or non-radiative deactivation. The overall fluorescence yield is the product of the yields of these different steps:

$$\phi_T = \phi_1 \times \phi_2 \times \phi_3$$

The last step is the deactivation of the emission level of the rare earth. It encompasses deactivations of different kinds which take place at different rates.

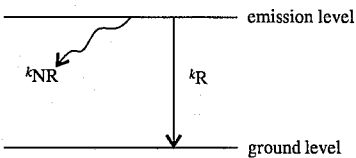

The yield of radiative deactivation of the emission level of the rare earth is expressed by the formula $$\phi_3 = \frac{k_R}{k_R + k_{NR}}$$

in which $k_R$ is the radiative deactivation rate and $k_{NR}$ is the sum of the non-radiative deactivation rates. The sum of these 2 deactivation rates is expressed by $k_D$.

In the case of transfer between a donor and an acceptor, the transfer efficiency is expressed by $$E = \frac{k_T}{k_T + k_R + k_{NR}} = \frac{k_T}{k_T + k_D}$$

In general, it is considered in the prior art that the transfer rate $k_T$ depends on the overall quantum yield $\phi_T$. This is indicated for example in D. Thomas et al., PNAS, 1978, 75, 5746–5750, by the relationship $$k_T = k_o (r/R_o)^{-6}$$

in which r is the distance between the donor and the acceptor, $R_o$ is the donor-acceptor distance at which the transfer efficiency is 50%, $R_o$ being a function of $Q_o$, which is the overall quantum yield.

In the case of phosphorescent tracer molecules, the deactivation mechanisms are analogous except that radiative deactivation takes place from the triplet level.

The luminescent acceptor compounds which can be used to obtain amplification of the emission signals of the luminescent donor compounds are chosen as a function of the latter and more precisely as a function of the yield of radiative deactivation of their emission level.

In fact, it has been found that amplification of the emission signal of the donor compound takes place when the relationship $$E\phi_A > \phi_3$$

in which

E is the transfer efficiency, $\phi_A$ is the quantum yield of the acceptor compound, $\phi_3$ is the yield of radiative deactivation of the emission level, is satisfied.

These variables can be expressed by the following formulae:

$$E = \frac{k_T}{k_T + k_D}$$

$$\phi_3 = \frac{k_R}{k_D}$$

$$k_T = k_R J R^{-6} K$$

in which

E, $k_T$, $k_R$ and $k_D$ are as defined above,

J is the overlap integral of the spectra,

R is the donor-acceptor distance in the test in question, and $k = n^{-4} \times 5.87 \times 10^{23}$, n being the refractive index of the medium, when R is expressed in Å and J in $cm^3 M^{-1}$.

E can therefore be expressed by the relationship $$E = \frac{1}{1 + \frac{1}{\phi_3 R^{-6} K J}}$$

The relationship $E\phi_A > \phi_3$ can be expressed by $$\frac{E}{\phi_3} > \frac{1}{\phi_A}$$

which can also be expressed by $$\frac{1}{\phi_3 + \frac{1}{R^{-6} K J}} > \frac{1}{\phi_A} \text{ or } \phi_A - \phi_3 > \frac{R^6}{KJ}$$

The relationship $$\phi_A - \phi_3 > \frac{R^6}{5.87 \cdot 10^{23} \times n^{-4} \times J}$$

therefore governs the choice of the acceptor compound as a function of the donor compound because the values $\phi_A$, $\phi_3$ and J are characteristic of the acceptor/donor pair.

The overlap integral of the spectra, J, is calculated as indicated in Conrad et al., Biochemistry, 1968, 7, 777–787.

The yield of radiative deactivation of the emission level, $\phi_3$, is calculated in the manner known in the literature, for example as described by N. Sabbatini et al. in Supramolecular Biochemistry, 1987, p. 187–206, Reidel Dordrecht, edited by V. Balzani.

The invention therefore relates to a method of amplifying the emission signal of a luminescent compound used as a donor compound in a luminescent assay, in which a luminescent acceptor compound is also used, wherein the luminescent donor compound possesses a low overall quantum yield and wherein the quantum yield of radiative deactivation of the emission level of the donor is lower than the quantum yield of the acceptor.

The luminescent donor compounds used in a luminescent assay will advantageously be compounds with a long lifetime, such as fluorescent rare earth cryptates or chelates or else phosphorescent molecules.

In a preferred feature, the invention relates to a method of amplifying the emission signal of a rare earth chelate or cryptate used as a luminescent donor compound in a luminescent assay, in which a luminescent acceptor compound is also used, wherein the rare earth chelate or cryptate possesses a low overall quantum yield and wherein the quantum yield of radiative deactivation of the emission level of the rare earth is lower than the quantum yield of the acceptor.

Another feature of the invention relates to a homogeneous luminescent method of detecting and/or determining an analyte in a medium in which it may be present, by revealing the product of the reaction of the analyte with at least one corresponding receptor, said method consisting in 1) adding to said medium a first reagent consisting of at least one receptor for said analyte, 2) adding a second reagent selected from the analyte or at least one of its receptors, one of the two reagents being coupled with a luminescent donor compound consisting of a rare earth chelate or cryptate and the other reagent being coupled with a luminescent acceptor compound, it being possible for the order of addition of the reagents to be reversed, and, after excitation of the mixture with a light source at the excitation wavelength of the luminescent donor compound, 3) measuring the emission signal of the luminescent acceptor compound, wherein the rare earth chelate or cryptate used as the donor compound possesses a low overall quantum yield and a yield of deactivation of the emission level of the rare earth which is lower than the quantum yield of the acceptor.

In the present description:

"analyte" is defined as any substance or group of analogous substances to be detected and/or determined;

"receptor" is defined as any substance capable of binding specifically to a site on said analyte;

"luminescent compound" is defined as any substance which, when excited at a given wavelength, is capable of emitting light.

In a preferred feature, the homogeneous method of detecting and/or determining an analyte in a medium in which it may be present, according to the invention, is an excess method consisting in 1) adding, to said medium containing the analyte being tested, a first reagent consisting of at least one receptor for said analyte, coupled with a luminescent donor compound consisting of a rare earth chelate or cryptate, 2) adding a second reagent consisting of one or more different receptors for said analyte, said second reagent being coupled with a luminescent acceptor compound, 3) incubating said medium after each addition of reagents or after the addition of the two reagents, 4) exciting the resulting medium at the excitation wavelength of the luminescent donor compound, 5) measuring the signal emitted by the luminescent acceptor compound.

In a preferred feature, a single receptor for the analyte, which is coupled either with the luminescent donor compound or with the luminescent acceptor compound, will be used in the above excess method.

In another feature, this method is a competitive method consisting in 1) adding, to said medium containing the analyte being tested, a first reagent consisting of a receptor for said analyte, coupled with a luminescent donor compound consisting of a rare earth chelate or cryptate, 2) adding a second reagent consisting of the analyte coupled with a luminescent acceptor compound, 3) incubating said medium after each addition of reagents or after the addition of the two reagents, 4) exciting the resulting medium at the excitation wavelength of the luminescent donor compound, 5) measuring the signal emitted by the luminescent acceptor compound.

The homogeneous method of detecting and/or determining an analyte, according to the invention, can also be applied to a competitive method consisting in 1) adding, to said medium containing the analyte being tested, a first reagent consisting of a receptor for said analyte, said receptor being coupled with a luminescent acceptor compound, 2) adding a second reagent consisting of the analyte coupled with a luminescent donor compound consisting of a rare earth chelate or cryptate, 3) incubating said medium either after the addition of each reagent or after the addition of the two reagents, 4) exciting the resulting medium at the excitation wavelength of the luminescent donor compound, 5) measuring the signal emitted by the luminescent acceptor compound.

In an advantageous feature, the first and second reagents used in the above-indicated methods of detecting and/or determining an analyte are added simultaneously to the medium containing the analyte being tested.

Chelates or cryptates of terbium, europium, dysprosium, samarium or neodymium will advantageously be used as luminescent donor compounds. A chelate or cryptate of terbium or europium will preferably be used.

In an advantageous feature, the rare earth cryptates which can be used in the methods according to the invention are described in European patent application 180 492. These compounds consist of at least one rare earth salt complexed by a macropolycyclic compound of the general formula

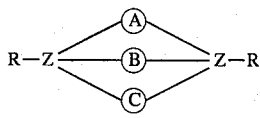

in which Z is a trivalent or tetravalent atom such as nitrogen, carbon or phosphorus, R is nothing, hydrogen, the hydroxyl group, an amino group or a hydrocarbon radical and the divalent radicals Ⓐ, Ⓑ and Ⓒ independently of one another are hydrocarbon chains which may or may not contain one or more heteroatoms and may or may not be interrupted by a heteromacrocycle, at least one of the radicals Ⓐ, Ⓑ or Ⓒ additionally containing at least one molecular unit or essentially consisting of a molecular unit, said molecular unit possessing a greater triplet energy than the emission level of the complexed rare earth ion.

Particularly preferred molecular units for the purposes of the invention are phenanthroline, anthracene, benzene, naphthalene, biphenyl and terphenyl, bipyridines and biquinolines, especially biisoquinolines, for example 2,2'-bipyridine, azobenzene, azopyridine, pyridine or 2,2'-biisoquinoline.

The following chains may be mentioned in particular as examples of radicals Ⓐ, Ⓑ and Ⓒ containing an energy donating unit:

$X_1$ and $X_2$, which can be identical or different, denoting oxygen, nitrogen or sulfur, and

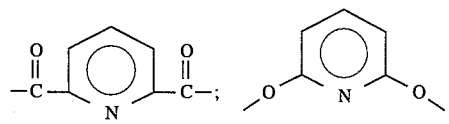

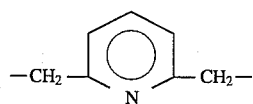

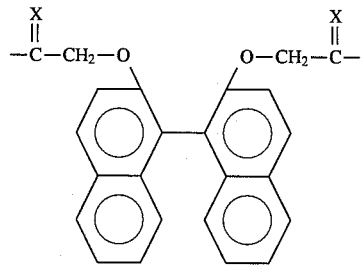

X being oxygen or hydrogen.

Compounds described in European patent application 0 180 492 which are preferably used in the method of the invention are the terbium cryptate Tb trisbipyridine and the europium cryptate Eu trisbipyridine.

Other rare earth cryptates which can be used in the method of the invention are described in European patent application 321 353. They consist of at least one rare earth salt complexed by a macropolycyclic compound of formula I or formula II below:

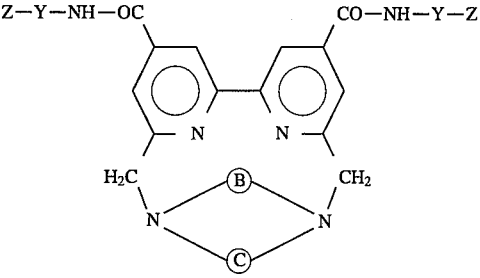

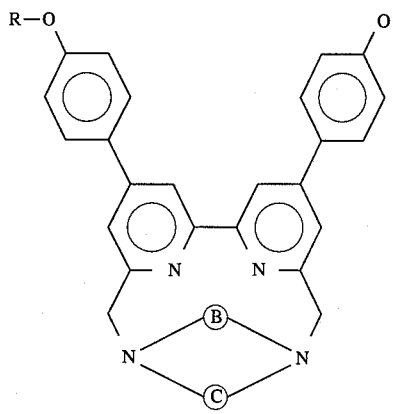

in which
the ring of the formula

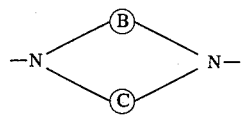

is one of the following rings:

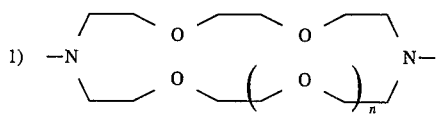

n = 0 or 1
[N₂O₄] macrocycle or (22) ring
[N₂O₃] macrocycle or (21) ring

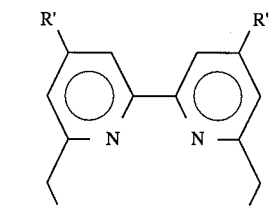

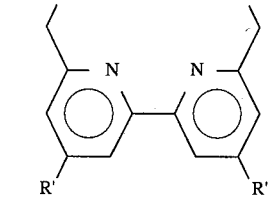

2)    bisbipyridine macrocycle

Y is a group or spacer arm which consists of a divalent organic radical selected from linear or branched $C_1$ to $C_{20}$ alkylene groups which may eventually contain one or more double bonds and/or may eventually be interrupted by one or more heteroatoms such as oxygen, nitrogen, sulfur or phosphorus, from $C_5$–$C_8$ cycloalkylene groups or from $C_6$ to $C_{14}$ arylene groups, said alkylene, cycloalkylene or arylene groups being unsubstituted or substituted by alkyl, aryl or sulfonate groups;

Z is a functional group capable of bonding covalently with a biological substance;

R is a methyl group or the group —Y—Z; and

R' is hydrogen or a group —COOR", in which R" is a $C_1$ to $C_{10}$ alkyl group and preferably the methyl, ethyl or tert-butyl group, or alternatively R' is a group —CO—NH—Y—Z.

Examples of appropriate functional groups which may be mentioned in particular are amino, thio, cyano, isocyano, isothiocyano, thiocyano, carboxyl, hydroxyl, maleimido, succinimido, mercapto, phenol, imidazole, aldehyde, epoxide, halide, thionyl, sulfonyl, nitrobenzoyl, carbonyl, triazo, anhydride, halogenoacetate, hydrazino and acridine groups etc.

The particularly preferred groups are amino, thio and carboxyl groups, which have to be activated prior to covalent coupling with the biological substance, and maleimido, succinimido and isothiocyanate groups, which can bind directly to the biological substance.

Compounds described in European patent application 321 353 which are advantageously used in the methods of the invention are the europium cryptate Eu trisbipyridinediamine and the terbium cryptate Tb trisbipyridinediamine.

The rare earth cryptates described above have the additional advantage of a long lifetime of the order of several tens of µs, making it possible on the one hand to use the time-resolved measurement technique and thus to neutralize the interference emissions, and on the other hand to use conventional equipment for the measurement.

Phosphorescent compounds such as eosine or erythrosine can also be used as luminescent donor compounds.

The luminescent acceptor compounds used in the methods of the invention are chosen as a function of the donor compounds, as indicated above.

If the luminescent donor compound is a fluorescent europium cryptate, it will be advantageous to use a fluorescent acceptor compound selected from allophycocyanine, allophycocyanine B, C phycocyanine or R phycocyanine.

In the case where a terbium cryptate is used as the donor compound, it will be advantageous to use a fluorescent acceptor compound selected from rhodamines, thionine, R phycocyanine, phycoerythrocyanine, C phycoerythrin, B phycoerythrin or R phycoerythrin.

A phosphorescent compound such as eosine or erythrosine can also be used as the luminescent donor compound. In this case, it will be advantageous to use a fluorescent acceptor compound selected from chlorophylls such as those mentioned in European patent applications 71 991 and 314 406, or porphyrins such as those mentioned in European patent application 71 991, or else phthalocyanines such as those of patent application PCT/WO 88 04777.

In the case of an assay in a liquid medium using phosphorescent donor compounds, the result will be evaluated either on a solid support or by the addition of oxygen absorbing molecules to the measuring medium, these techniques being known to those skilled in the art.

Chlorophylis and phthalocyanines can also be used as fluorescent acceptor compounds with a europium chelate or cryptate as the donor compound.

A modulated light source such as those described in Lakowicz, Principles of fluorescent spectroscopy, Plenum Press, New York, 1983, p. 96–100, will advantageously be used as the light source permitting excitation of the luminescent donor compound.

In particular, the amplification method of the invention has an important application in fluorescent immunoassays, in both the so-called competitive and excess assay methods, in the homogeneous or heterogeneous phase, which are described in the prior art (Landon, Ann. Clin. Biochem. 1981, 18, 253, and E. SOINI et al., Clin. Chem. 1979, 25, 353).

In particular, the amplification method of the invention can advantageously be used in immunoassays in a serum medium which require a high sensitivity, this normally being affected by a substantial background.

In fact, the amplification method of the invention makes it possible to use tracers which have a low overall quantum yield and whose residual signal is therefore also weaker.

The invention will be understood more clearly with the aid of the following Examples, which do not in any way imply a limitation.

EXAMPLE 1

Two series of dynamic amplification tests were performed, on the one hand using the europium cryptate Eu trisbipyridine (EuTBP), prepared as described in European patent application 180 492 (Example 5), as the donor compound and allophycocyanine (Interchim, France) as the acceptor compound, and on the other hand using the terbium cryptate Tb trisbipyridine (TbTBP), prepared analogously to Eu trisbipyridine, as the donor compound and rhodamine B (Fluka, Switzerland) or B phycoerythrin (Sigma, USA) as the acceptor compound.

The donor compound is used at a concentration of $10^{-8}$ mol/l in different buffers:

0.1M phosphate buffer of pH 7.4

0.1M Tris buffer of pH 8

0.1M Tris HCl buffer of pH 7.1 these buffers also containing 1 g/l of human serum albumin, in the presence of different concentrations of acceptor compound. The fluorescence can be measured by the time-resolved method by means of an ARCUS fluorimeter (LKB, Sweden) using an interference filter adapted to the emission of the acceptor compound.

The time-resolved measurement of the fluorescence was carried out in the present test using a prototype laser fluorimeter, which is described below:

A nitrogen pulsed laser (LASER SCIENCE INC., model LS1-337ND) is used as the excitation source (wavelength at 337.1 nm). The duration of the pulses is specified at 3 nanoseconds and is repeated at a frequency of 10 Hertz. The beam passes through a filter (CORNING) so as to eliminate any light interfering with the excitation, other than 337 nm.

After entering the measuring chamber, the beam is reflected by a dichroic filter, placed at 45 degrees, which has the property of reflecting the ultraviolet and being able to transmit the visible light.

The beam reflected by the dichroic filter is focused by a fused silica lens on to the well to be measured in a microplate. The fluorescence emission is collected at a solid angle of 20 degrees, collimated by the same lens, and passes directly through the dichroic filter (visible light fluorescence).

An interference filter, whose characteristics are defined according to the fluorescence wavelength to be detected, makes it possible to eliminate the light capable of interfering with the signal, the intensity of which is then measured by a photomultiplier (HAMAMATSU R2949).

The photon counter used is an SR-400 (STANFORD RESEARCH SYSTEMS) and its operations and synchronization with the laser are controlled by a computer of the IBM PC-AT type via an RS 232 output. The pulses coming from the photomultiplier are recorded during a given time gate ($t_g$) and after a given delay ($t_d$) provided said pulses are above a discriminating level selected by the photon counter so as to optimize the signal-to-noise ratio of the photomultiplier.

An X-Y plotter, driven by the IBM PC-AT, enables the microplate which is being measured to adopt different positions through the action of stepping motors, these positioning operations including the maneuvers for charging, positioning under the exciting beam, automatic sequential evaluation of the 96 wells, and removal of the microplate.

Either 200 μl of working buffer or 200 μl of the following solutions:

allophycocyanine at $1.24.10^{-5}$M in working buffer p
rhodamine B at $2.10^{-5}$M, $1.6.10^{-5}$M or $1.2.10^{-5}$M in 0.1M Tris HCl buffer of pH 7.1
B phycoerythrin at $1.54.10^{-6}$M or $9.6.10^{-7}$M in 0.1M Tris HCl buffer of pH 7.1
are added to 200 μl of a $2.10^{-8}$M solution of EuTBP or TbTBP in the working buffer.

To determine the amplification, the fluorescence was measured in a first stage for the donor compound alone by measurement of the area of the peak emitted at 620 nm with an interference filter having a transmission factor of 80% and a width at half height of 20 nm for EuTBP, and at 545 nm with a filter having a transmission factor of 80% and a width at half height of 20 nm for TbTBP.

In a second stage, the fluorescence of the mixture is determined after excitation at 307 nm and measured in the same way but at 670 nm for the donor compound in the presence of the acceptor compound (allophycocyanine) and at 580 nm (rhodamine, B phycoerythrin).

The result is evaluated after delays of 0.1 and 0.05 ms. The lifetime of the emitted signals is also measured.

The results are as follows:

| | τ ms | Signal $t_d$ = 0.1 ms | A | Signal $t_d$ = 0.05 ms | A |
|---|---|---|---|---|---|
| 1) Eu trisbipyridine in a 0.1 M phosphate buffer of pH 7.4 | | | | | |
| Allophycocyanine | | | | | |
| 0 | 0.6 | 40 | 1 | 43.5 | 1 |
| $6.2.10^{-6}$ M | 0.13 | 52.5 | 1.3 | 77 | 1.8 |
| 2) Eu trisbipyridine in a 0.1 M Tris buffer of pH 8 | | | | | |
| Allophycocyanine | | | | | |
| 0 | 0.34 | 22.5 | 1 | 26 | 1 |
| $6.2.10^{-6}$ M | 0.1 | 54 | 2.4 | 90 | 3.5 |
| 3) Tb trisbipyridine in a 0.1 M Tris HCl buffer of pH 7.1 | | | | | |
| Rhodamine B | | | | | |
| 0 | 0.34 | 31 | 1 | 36 | 1 |
| $10^{-5}$ M | 0.086 | 106 | 3.4 | 190 | 5.3 |
| $8.10^{-6}$ M | 0.095 | 95 | 3 | 162 | 4.5 |
| $6.10^{-6}$ M | 0.115 | 85 | 2.7 | 132 | 3.7 |
| 4) Tb trisbipyridine in a 0.1 M Tris HCl buffer of pH 7.1 | | | | | |
| B Phycoerythrin | | | | | |
| 0 | 0.34 | 31 | 1 | 36 | 1 |
| $7.7.10^{-7}$ M | 0.124 | 142 | 4.6 | 214 | 5.9 |
| $4.8.10^{-7}$ M | 0.174 | 152 | 4.9 | 200 | 5.5 |

τ = lifetime of the emitted signal
$t_d$ = evaluation delay
A = amplification

The results show that in all cases there is amplification of the signal emitted by the acceptor compound compared with that of the donor compound alone. This amplification varies from 1.8 to 5.9.

EXAMPLE 2

A dynamic amplification test was performed in the same way as described in Example 1 using the europium cryptate Eu trisbipyridine (prepared according to Example 5 of European patent application 180 492) as the donor compound at a concentration of $10^{-8}$ mol/l, and allophycocyanine (Cyanotech, USA) as the acceptor compound at a concentration of $6.2.10^{-6}$M, in water or 0.1M phosphate buffer of pH 7.4.

In a first stage, the deactivation yield of the rare earth ($\phi_3$ Eu) was determined in the 2 buffers used, according to the formula $$\phi_3 Eu = \frac{\tau}{\tau_{77}}$$

in which

τ is the lifetime of the europium cryptate Eu trisbipyridine, measured under the experimental conditions, $\tau_{77}$ is the lifetime of this cryptate in heavy water at 77° K. (liquid nitrogen).

Also, the overall quantum yield (φ total) is determined by a conventional method, for example as described in Lakowicz, Principles of fluorescent spectroscopy, Plenum Press, New York, 1983.

The time-resolved measurement of the fluorescence was then carried out by means of the prototype laser fluorimeter described in Example 1, the cryptate Eu trisbipyridine and allophycocyanine being brought into contact as indicated in Example 1. The transfer efficiency was calculated according to the reference D. Thomas et al., P.N.A.S. 1978, 75, 5746–5750, by the formula $E=1-\tau/\tau_o$, in which τ is the lifetime of the donor in the presence of the acceptor and $\tau_o$ is the lifetime of the donor alone.

The results are reported in Table I below:

TABLE I

| Medium | φ total | $\phi_3$ Eu | Transfer efficiency with $6.2.10^{-6}$ M allophycocyanine |
|---|---|---|---|
| 0.1 M Tris buffer of pH 8 | 2% | 23% | 70% |
| 0.1 M phosphate buffer of pH 7.4 | 4% | 39% | 80% |

These results show that when using a donor compound having a low total quantum yield, it is nevertheless possible to obtain a high transfer efficiency, which brings about amplification of the signal of the donor compound.

EXAMPLE 3

A dynamic amplification test was performed under the conditions of Example 1 using the terbium cryptate Tb trisbipyridine, prepared as described in European patent application 180 492, as the donor compound and B phycoerythrin (Sigma, USA) or rhodamine B (Fluka, Switzerland) as the acceptor compound in order to determine the acceptor concentration which made it possible to obtain a transfer efficiency of 50%.

The terbium chelate $Tb(DPA)_3$ described in D. Thomas et al., P.N.A.S. 1978, 75, 5746–5750, which possesses a quantum yield of 100%, was used as the reference.

The results show that the concentrations of acceptor (B phycoerythrin or rhodamine B) which make it possible to obtain a transfer efficiency of 50% using the terbium cryptate Tb trisbipyridine, whose quantum yield is about 2%, as the donor are of the same order ($6.10^{-7}$M) as the concentrations measured using the terbium chelate Tb(DPA)$_3$, whose quantum yield is about 100%.

This brings about amplification of the signal of the donor Tb trisbipyridine.

EXAMPLE 4

Assay of Prolactin

A homogeneous immunoassay showing the application of the principle of amplification to the assay of prolactin was performed using the europium cryptate Eu trisbipyridinediamine, prepared as described in European patent application 321 353 (Examples 3 and 4), as the donor compound and allophycocyanine (Cyanotech, USA) as the acceptor compound, coupled respectively with the anti-prolactin monoclonal antibodies E$_1$ and 3D3 (CIS bio international, France) recognizing 2 different epitopes of prolactin.

The following abbreviations are used below:

APC=allophycocyanine
DTT=dithiothreitol
EuTBP=the europium cryptate Eu trisbipyridinediamine
HSA=human serum albumin
IgG=immunoglobulin G
SPDP=N-succinimidyl 3-(pyridyl-2-dithio)propionate
sulfo-SMCC=sulfosuccinimidyl 4-(N-maleimidomethyl-)cyclohexane- 1-carboxylate

1) PREPARATION OF IgG 3D3-APC a) Activation of APC with sulfo-SMCC

APC (3 mg), supplied commercially in precipitated form in a 60% solution of ammonium sulfate, is centrifuged. After removal of the supernatant, the residue is taken up with 250 μl of 100 mM phosphate buffer of pH 7.0 and then filtered at 0.8 μm to remove any suspended particles.

The filtrate is purified by exclusion chromatography on a G25 superfine column (Pharmacia, Sweden) in the same buffer. The concentration of APC eluted in the exclusion volume is determined at 650 nm with an $\epsilon_{650nm}$ of 731,000M$^{-1}$cm$^{-1}$.

The APC is activated by adding a solution of sulfo-SMCC prepared for immediate use at a concentration of 6.9 mM in a 100 mM phosphate buffer of pH 7.0, and by allowing the reaction to proceed for one hour at room temperature, with gentle stirring (molar ratio of 15 to 75 sulfo-SMCC per APC). The APC-maleimide is then purified on a G25 superfine column in 100 mM phosphate, 5 mM EDTA buffer of pH 6.5 and stored at 4° C. before coupling with IgG 3D3.

b) Activation of IgG 3D3 with SPDP

Simultaneously, 5 mg of IgG 3D3 at a concentration of 10 mg/ml in a 100 mM phosphate buffer of pH 7.0 are activated by the addition of a solution of SPDP (Pierce, USA) at a concentration of 6.4 mM in dioxane, in a molar ratio of 7.5 SPDP per IgG 3D3.

After activation for 35 min at room temperature, the IgG pyridine-2-thione is purified on a G25 superfine column in a 100 mM phosphate, 5 mM EDTA buffer of pH 6.5.

The proteins are concentrated and the pyridyl- 2-disulfide groups are reduced with a solution of DTT (Sigma, USA) having a final concentration of 19 mM, for 15 min at room temperature. The DTT and the pyridine- 2-thione are removed by purification on a G25 superfine column in 100 mM phosphate, 5 mM EDTA buffer of pH 6.5. The concentration of IgG-SH is determined at 280 nm with an $\epsilon_{280nm}$ of 210,000M$^{-1}$cm$^{-1}$.

c) Conjugation of IgG 3D3-SH with APC-maleimide

The thiol groups are bound to the maleimides by adding 2.51 mg of activated APC per mg of IgG 3D3-SH. After incubation for 18 hours at 4° C. in the dark, with gentle stirring, the thiol groups which have remained free are blocked by the addition of a 100 mM solution of N-methylmaleimide (Sigma, USA) having a final concentration of 20 mM, for one hour at room temperature.

The reaction medium is purified by gel filtration on a TSK G3000SW semipreparative column (Beckmann, USA) in 100 mM phosphate buffer of pH 7.0.

The concentrations of APC and IgG 3D3 in the purified conjugate, eluted in the first peak, are determined by the absorptions at 280 nm and 650 nm according to the following calculation:

$$[APC]_{mol/l} = A_{650nm}/710,000$$

$$[IgG]_{mol/l} = (A_{280nm} - A'_{280nm})/210,000$$

where A'$_{280nm}$ is the contribution of the APC-maleimide at this wavelength, as determined above (section 1-a)).

Human serum albumin (HSA) is added in an amount of 1 g/l to the conjugate, which is then divided up into aliquots and frozen at −20° C.

2) PREPARATION OF THE CONJUGATES IgG E$_1$-EuTBP

IgG E$_1$-SH is prepared by the protocol described above for the IgG 3D3 except that the molar ratio is varied from 4 to 16 SPDP per IgG E$_1$.

A 25 mM solution of sulfo-SMCC in 20 mM phosphate, 10% (v/v) dimethylformamide buffer of pH 7.0 is added to 5 mg ($5.10^{-6}$ mol) of EuTBP in a proportion of 2.5 mol of activator per mol of EuTBP.

After activation for 45 min at room temperature, the reaction medium is filtered at 0.8 μm to remove any precipitate formed. The undesired reaction products (sulfo-SMCC, N-hydroxysuccinimide, (N-maleimidomethyl)carboxylic acid) are removed by ion exchange chromatography on a Mono Q column (Pharmacia, Sweden) in 20 mM phosphate, 10% (v/v) dimethylformamide buffer of pH 7.0 under NaCl shock. The concentration of EuTBP-maleimide is determined at 307 nm with an $\epsilon_{307nm}$ of 25,000M$^{-1}$cm$^{-1}$ and the ratio $A_{307nm}/A_{280nm}$ is also determined.

In a manner similar to that described above, the maleimide groups are reacted with the thiol groups bound to the antibody, in molar proportions varying from 10 to 30 EuTBP-maleimide per IgG E$_1$-SH.

After incubation for 18 hours at 4° C. and blocking of the thiol groups (which may have remained free) with N-methylmaleimide, the non-coupled EuTBP is removed by dialysis in 100 mM phosphate buffer of pH 7.0, at 4° C., until it is exhausted (no further fluorescence in the dialysis baths).

The characteristics of the conjugate are determined by its absorptions at 307 nm and 280 nm using the following values and allowing for the intrinsic absorption of the cryptate, determined by the ratio $A_{307nm}/A_{280nm}$:

EuTBP-maleimide:
$\epsilon_{307nm} = 25,000 M^{-1} cm^{-1}$
$A_{307nm}/A_{280nm}$: determined experimentally IgG $E_1$-SH:
$\epsilon_{280nm} = 210,000 M^{-1} cm^{-1}$
$\epsilon_{307nm} = 0 M^{-1} cm^{-1}$

3) APPLICATION TO THE ASSAY OF PROLACTIN

The following are added successively to 350 µl 96-well polystyrene microplates (Dynatech, USA):

100 µl of standard prolactin solution of known concentration

100 µl of IgG $E_1$-EUTBP conjugate (donor) at 0.5 µg/ml

100 µl of IgG 3D3-APC conjugate (acceptor) at 3 µg/ml

The two conjugates are diluted in 50 mM phosphate, 1 g/l HSA buffer of pH 7.4.

After incubation for one hour at room temperature, the result is evaluated by means of the (prototype) laser fluorimeter described in Example 1, equipped with a 650 nm filter of width 20 nm, with a delay of 50 µs and for 100 µs.

The results obtained, expressed in counts per second (cps), are reported in Table II below:

TABLE II

|  |  | cps | Δ cps |
|---|---|---|---|
| HSA buffer |  | 4890 |  |
| prolactin | 0 | 9579 | 0 |
|  | 1200 µU | 13,638 | 4059 |
|  | 3000 µU | 17,638 | 8059 |
|  | 6500 µU | 23,108 | 13,529 |

These results show that the measured signal resulting from the donor-acceptor transfer varies proportionately to the concentration of prolactin in the medium.

The donor compounds having a low quantum yield, according to the invention, are therefore particularly suitable for this type of immunoassay.

EXAMPLE 5

Assay of Prolactin

Another assay was performed analogously to that described above in Example 4, section 3), using a different acceptor compound: C phycocyanine (Cyanotech, USA).

The following are added successively to 350 µl 96-well polystyrene microplates (Dynatech, USA):

100 µl of standard prolactin solution of known concentration

100 µl of IgG $E_1$-EuTBP conjugate (donor) at 0.1 or 0.5 µg/ml

100 µl of IgG 3D3-phycocyanine conjugate at 3 µg/ml

The two conjugates are diluted in 50 mM phosphate, 1 g/l HSA buffer of pH 7.4.

The measurement is carried out after incubation for one hour at room temperature by means of the laser fluorimeter described in Example 1, equipped with a 647 nm filter of width 20 nm.

The results are given in Table III below and expressed in counts per second (cps):

TABLE III

|  |  | cps | Δ cps |
|---|---|---|---|
| HSA buffer |  | 4890 |  |
| IgG $E_1$-EuTBP 0.1 g/ml |  |  |  |
| Prolactin | 0 | 5543 | 0 |
|  | 250 µU | 6525 | 982 |
|  | 1000 µU | 7731 | 2188 |
|  | 10,000 µU | 8595 | 3052 |
| IgG $E_1$-EuTBP 0.5 g/ml |  |  |  |
| Prolactin | 0 | 9266 | 0 |
|  | 250 µU | 10,359 | 1086 |
|  | 1000 µU | 15,010 | 5744 |
|  | 10,000 µU | 22,805 | 13,539 |

These results again show that the measured signal resulting from the donor-acceptor transfer varies proportionally to the quantity of prolactin present in the medium.

EXAMPLE 6

Assay of Antigen 19.9

Antigen 19.9 is a carbohydrate representative of the colon carcinoma.

As the site of the anti-19.9 antibody is a repetitive epitope, the same antibody is labeled either with the donor or with the acceptor.

Antibody-EuTBP and antibody-APC conjugates, prepared analogously to the method described in Example 4, are used for this homogeneous immunoassay.

The antigen 19.9 and the anti-19.9 antibody are supplied by Centochor, USA.

The two conjugates are diluted in a 100 mM phosphate, 150 mM NaF, 1 g/lHSA buffer of pH 6.

A range of antigen 19.9 standards is produced by diluting a concentrated solution of antigen in newborn calf serum.

The following are added successively to 96-well polystyrene microplates (Dynatech, USA):

50 µl of standard solution of antigen 19.9

50 µl of dilution buffer

100 µl of antibody-EuTBP conjugate at 0.5 µg/ml

100 µl of antibody-APC conjugate at 5 µg/ml

After incubation for 3 h 30 min at room temperature, the result is evaluated by means of the laser fluorimeter described in Example 1, equipped with a 650 nm filter of width 20 nm, with a delay of 50 µs and for 400 µs.

The results are reported in Table IV below and expressed in arbitrary units (AU).

TABLE IV

| Antigen 19.9 u/ml | Signal AU |
|---|---|
| 0 | 312 |
| 9 | 419 |
| 30 | 572 |
| 64 | 890 |
| 138 | 1602 |
| 278 | 2491 |

These results show that the measured signal varies proportionally to the quantity of antigen 19.9 in the medium.

EXAMPLE 7

Assay of Carcinoembryonic Antigen (CEA)

Two monoclonal antibodies, G12 and G15 (CIS bio international, France), coupled respectively with the europium cryptate EuTBP and allophycocyanine, are used in this homogeneous immunoassay.

The two conjugates, G12-EuTBP and G15-APC, are diluted in a 100 mM phosphate, 1 g/l HSA, 150 mM NaF buffer.

The following are added successively to polystyrene microplates (Dynatech, USA):

100 μl of standard solution

100 μl of G12-cryptate conjugate at 0.5 μg/ml

100 μl of G15-APC conjugate at 5 μg/ml

After incubation for 3 h at 37° C., the result is evaluated by means of the laser fluorimeter described in Example 1, equipped with a 650 nm filter of width 20 nm, with a delay of 50 μs and for 400 μs.

The results obtained are reported in Table V below and expressed in arbitrary units (AU):

TABLE V

| CEA ng/ml | Signal AU |
|---|---|
| 0 | 345 |
| 5.9 | 420 |
| 21 | 474 |
| 72 | 769 |
| 2634 | 1058 |

The results show that the emitted signal varies proportionally to the concentration of CEA. Furthermore, the amplification of the signal enables the CEA to be detected with a sensitivity of the order of ng/ml.

EXAMPLE 8

Assay of Digoxin

Digoxin is a cardiotonic glycoside used as the active principle of drugs for treating cardiac insufficiency.

A/Preparation of an allophycocyanine-digoxin Tracer by Coupling with Periodate a) Activation of digoxin with periodate 268 μl of a solution of $NaIO_4$ (Fluka, Switzerland) prepared for immediate use are added to a suspension of digoxin (ref. 37100 Fluka, Switzerland) containing 5.35 mg in 268 μl of absolute ethanol.

The mixture is incubated for 20 min at room temperature, with agitation, and the reaction is then blocked by the addition of 100 μl of 0.1M glycerol.

The final concentration of activated digoxin, calculated on the basis of the initial mass and the final volume, is $1.2 \times 10^{-2}$M.

b) Coupling of activated digoxin with allophycocyanine (APC)

95 μl of the solution of digoxin activated with periodate are added to 2 ml of purified APC solution (Cyanotech, USA) in borate buffer of pH 9.0.

The mixture is incubated for 1 h 30 min at room temperature, with gentle stirring. The reaction is blocked by the addition of 100 μl of a solution of sodium borohydride prepared for immediate use at a concentration of 5 mg of $NaBH_4$ in 1.32 ml of borate buffer of pH 9.0.

c) Purification of the APC-digoxin tracer 2 ml of the reaction mixture are injected on to an HR 10/10 G25 column (Pharmacia, Sweden) equilibrated in 100 mM phosphate buffer of pH 7, and eluted in the excluded volume. The excess reagents are eluted with 8 ml of buffer.

About 4 ml of a solution of the APC-digoxin coupled product containing 1.22 mg/ml of APC (measured by the absorbance at 650 nm) are recovered.

The concentration of digoxin is evaluated by an RIA or DELFIA (Pharmacia, Sweden).

The calculated final molar ratio digoxin/allophycocyanine is about 0.8.

B/Competitive Homogeneous Assay of Digoxin in Human Serum

A conjugate of antibody and the europium cryptate EuTBP diamine is prepared analogously to the method described in Example 1 using an anti-digoxin mouse monoclonal antibody (ref. G 31604 M, Interchim, France). This antibody-cryptate conjugate is used at a concentration of 0.5 μg/ml in 100 mM phosphate, 150 mM NaF, 1 g/l HSA buffer of pH 7.

The APC-digoxin tracer is used at a concentration of 0.2 μg/ml in the same buffer.

A range of digoxin standards is prepared by diluting, in human serum, a solution of digoxin (Fluka, Switzerland) containing 1 mg/ml in a 50/50 ethanol/water mixture.

The standard curve is produced by taking 250 μl samples containing

50 μl of phosphate buffer

50 μl of standard

100 μl of APC-digoxin tracer

100 μl of antibody-cryptate conjugate

The samples to be cryptate are made up in the same way, the 50 μl of standard being replaced with 50 μl of individual serum to be assayed.

The assay is performed in 96-well microplates (Dynatech, USA).

After incubation for 30 min at room temperature, the result is evaluated on a laser fluorimeter as described in Example 1, equipped with a 665 nm filter having a width at half height of 20 nm, in a time gate of 100 μs and after a delay of 50 μs.

The results are expressed as a percentage of the ratio $B/B_o$, in which B is the value obtained for each standard and $B_o$ is that of the standard 0.

The results obtained are reported in Table VI below:

TABLE VI

| Digoxin standard ng/ml | $B/B_o$ % |
|---|---|
| 0 | 100 |
| 1.6 | 96.21 |

TABLE VI-continued

| Digoxin standard ng/ml | $B/B_o$ % |
|---|---|
| 3.2 | 87.15 |
| 6.4 | 73.57 |
| 12.8 | 56.24 |
| 26 | 48.86 |

These results show that the values obtained vary proportionally to the concentration of digoxin.

EXAMPLE 9

Assay of Thyroxine

A/Preparation of an Allophycocyanine-Thyroxine (APC-$T_4$) Tracer a) Activation of thyroxine with S-AMSA 500 µl of a solution of S-AMSA (Sigma, USA) containing 8.7 mg/ml (50 mM) in methanol are added to 500 µl of a solution containing 20 mg/ml of $T_4$ (Calbiochem, France) in methanol, the mixture is incubated for 15 min at room temperature and 500 µl of a solution of hydroxylamine containing 6.95 mg/ml (100 mM) in methanol are then added. After incubation for 15 min at room temperature, 975 µl of the reaction mixture are removed and treated with 525 µl of double-distilled water filtered on a MILLIPORE HA 0.45 µm filter. This solution is passed in 250 µl fractions over a Pep. RPC HR 5/5 HPLC column (Pharmacia, Sweden) and eluted with a 65/35 methanol/water mixture. The first three peaks eluted are recovered and the successive fractions are pooled and evaporated under vacuum on a rotary evaporator. About 3 mg of activated $T_4$ ($T_4$-SH) are recovered.

b) Activation of allophycocyanine with SMCC 10 mg of APC are purified and then concentrated on an AMICON CENTRICON 30 cone to a concentration of 10.6 mg/ml in a volume of 700 µl.

160 µl of a solution of sulfo-SMCC (Pierce, USA) containing 10 mg/ml in a 100 mM phosphate buffer of pH 7 are added to the above solution. The reaction mixture is incubated for 1 h at room temperature, with agitation, and the activated APC is then purified by exclusion chromatography on a G 25 HR 10/10 column (Pharmacia, Sweden) in phosphate buffer of pH 7.

c) Coupling of activated thyroxine with activated allophycocyanine

The contents of the $T_4$-SH flask are taken up with 200 µl of methanol, and 50 µl of this solution are added to 2 ml of the solution of activated APC in 100 mM phosphate buffer of pH 7. The reaction mixture is incubated for 18 h at 4° C., with agitation, and the excess maleimide sites are then blocked with 5 µl of a solution of mercaptoethanol (Sigma, USA) at a concentration of 1/10 in phosphate buffer.

d) Purification of the APC-$T_4$ tracer

The reaction mixture is concentrated to a volume of 1 ml on an AMICON CENTRICON 30 ultrafiltration device and 50 µl of a solution of N-AANS containing 1 mg/ml in phosphate buffer are then added (final concentration of N-AANS about 50 µg/ml). The tracer is finally purified on a PHARMACIA G 25 HR 10/10 exclusion chromatography column (100 mM phosphate elution buffer of pH 7). This gives about 2.5 ml of tracer at a concentration of 0.8 mg/ml (calculated by the OD at 650 nm, $\epsilon$=731,000).

The number of molecules of $T_4$ coupled per molecule of APC is evaluated by RIA of the tracer and comparison with a standard $T_4$ curve ($R_4$-KPR kit, ORIS Industrie, France). The calculation gives a ratio over the purified tracer of 1.4 $T_4$/APC.

The APC-$T_4$ tracer is purified in the presence of N-AANS synthesized from N-ANS (KODAK, USA) by a modification of the protocol described by HINDS et al. (CLIN. CHEM. 32, 16–21, 1986).

B/Competitive Homogeneous Assay of Thyroxine in Human Serum

A conjugate of antibody and the europium cryptate EuTBP diamine is prepared analogously to the method described in Example 1 using the anti-$T_4$ mouse monoclonal antibody $R_{41}$ (CIS bio international, France). This conjugate is used at a concentration of 2 µg/ml in 100 mM phosphate, 120 mM NaF, 0.2% HSA buffer of pH 7.

A range of $T_4$ standards is prepared by dilution in a normal human serum treated by ion exchange and devoid of $T_4$. The standard curve is produced by taking 250 µl samples containing 50 µl of N-AANS solution 50 µl of human serum devoid of $T_4$ or 50 µl of one of the $T_4$ standards 100 µl of APC-$T_4$ tracer 100 µl of antibody-cryptate conjugate The samples to be assayed are made up in the same way, the 50 µl of standard being replaced with 50 µl of the individual serum to be assayed.

The assay is performed in 96-well microplates (Dynatech, USA).

After incubation for 30 min at room temperature, the result is evaluated on a laser fluorimeter as described in Example 1, equipped with a 665 nm filter having a width at half height of 20 nm, using a 1000 Hz flash lamp as the excitation source for 1 s, in a time gate of 100 µs and after a delay of 50 µs.

The values obtained for each standard (B) are divided by the value of the standard 0 ($B_o$) and expressed as a percentage ($B/B_o$%). The concentration of the samples to be assayed is calculated by comparison with the standard curve.

The results are reported in Table VII below:

TABLE VII

| Thyroxine ng/ml | $B/B_o$ % |
|---|---|
| 0 | 100 |
| 10 | 91 |
| 20 | 82.6 |
| 50 | 61.7 |
| 100 | 43.3 |
| 250 | 23 |

The results show that the values obtained vary proportionally to the concentration of $T_4$.

What is claimed is:

1. A homogenous luminescent method of detecting and/or determining an analyte in a medium in which it may be present, said method comprising the steps of:

1) adding to said medium a first reagent consisting of at least one receptor which specifically binds to said analyte, 2) adding a second reagent selected from the analyte or at least one receptor which specifically binds to the analyte; one of said first or second reagents being coupled with a luminescent donor compound consisting of a rare earth chelate or cryptate of terbium or europium, and the other reagent being coupled with a luminescent acceptor compound, wherein steps 1) and 2) may be reversed, 3) exciting the mixture with a light source at the excitation wavelength of the luminescent donor compound, 4) measuring the emission signal of the luminescent acceptor compound, wherein the rare earth chelate or cryptate of terbium or europium used as the donor compound possesses a low overall quantum yield and the yield of radiative deactivation of the emission level of the rare earth ion of terbium or europium in the chelate or cryptate is lower than the quantum yield of the acceptor and wherein the transfer efficiency between said luminescent donor compound and said luminescent acceptor compound times the quantum yield of the acceptor compound is greater than the yield of radiative deactivation of the emission level of the rare earth ion in the chelate or cryptate, whereby the emission signal of the rare earth chelate or cryptate of terbium or europium is amplified, and 5) correlating the measured emission signal of the luminescent acceptor compound to the presence and/or amount of analyte.

2. A method according to claim 1 wherein the first and second reagents are added simultaneously to the medium containing the analyte being tested.

3. A method according to claim 1 which comprises using a single receptor which specifically binds to the analyte.

4. A method according to claim 1 wherein the donor compound is a europium or terbium cryptate consisting of at least one europium or terbium salt complexed by a macrocyclic compound of the general formula

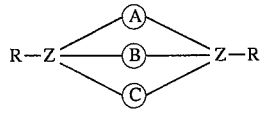

in which Z is nitrogen, carbon, or phosphorous, R is present or absent, and when present is hydrogen, an hydroxyl group, an amino group or a hydrocarbon radical and the divalent radicals Ⓐ, Ⓑ, and Ⓒ independently of one another are hydrocarbon chains which may or may not contain one or more heteroatoms and may or may not be interrupted by a heteromacrocycle, at least one of the radicals Ⓐ, Ⓑ, and Ⓒ additionally containing at least one molecular unit or essentially consisting of a molecular unit, said molecular unit possessing a greater triplet energy than the emission level of the uncomplexed europium or terbium.

5. A method according to claim 1 wherein the europium or terbium cryptate compound is complexed by a macropolycyclic compound of the general formula

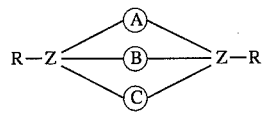

in which Ⓐ, Ⓑ and Ⓒ are independently selected from:

—C$_2$H$_4$—X$_1$—C$_6$H$_4$—X$_2$—C$_2$H$_4$— or

—C$_2$H$_4$—X$_1$—CH$_2$—C$_6$H$_4$—CH$_2$—X$_2$—C$_2$H$_4$—;

wherein X$_1$ and X$_2$, are identical or different, and are selected from the group consisting of oxygen, nitrogen, sulfur,

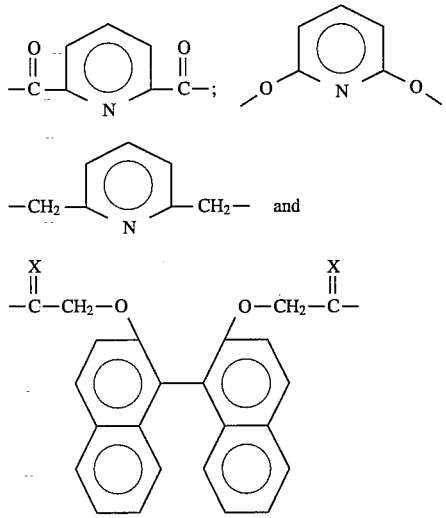

X being oxygen or hydrogen.

6. A method according to claim 1 wherein the donor compound is the terbium cryptate Tb trisbipyridine or the europium cryptate Eu trisbipyridine.

7. A method according to claim 3 wherein the luminescent donor compound is a europium or terbium cryptate consisting of at least one europium or terbium salt complexed by a macropolycyclic compound of formula I or II:

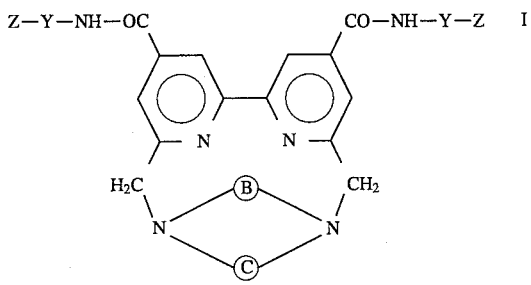

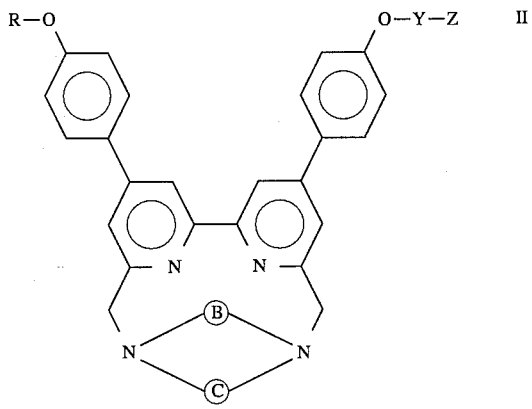

in which the ring of the formula

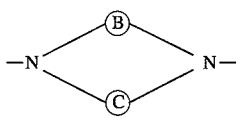

is one of the following rings

1) 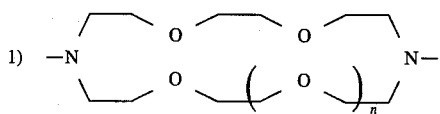

n = 0 or 1 or

2) 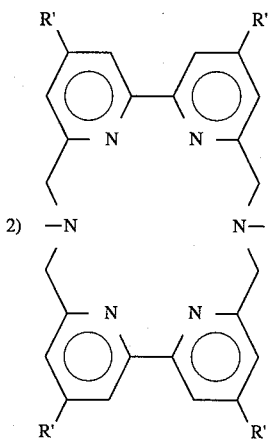

wherein R' is hydrogen; —COOR", in which R" is selected from a $C_1$ to $C_{10}$ alkyl group; or —CO—NH—Y—Z;

Y is a group or spacer arm which consists of a divalent organic radical selected from linear or branched $C_1$ to $C_{20}$ alkylene groups which may or may not contain one or more double bonds and/or may or may not be interrupted by one or more heteroatoms selected from oxygen, nitrogen, sulfur or phosphorus; $C_5$-$C_8$ cycloalkylene groups; or $C_6$ to $C_{14}$ arylene groups, said alkylene, cycloalkylene or arylene being unsubstituted or substituted by alkyl, aryl, or sulfonate groups;

Z is a functional group capable of bonding covalently with a biological substance; and R is a methyl group or the group —Y—Z.

8. A method according to claim 1 wherein the fluorescent donor compound is am europium cryptate and wherein the fluorescent acceptor compound is allophycocyanine, allophycocyanine B, C phycocyanine or R phycocyanine.

9. A method according to claim 1 wherein the fluorescent donor compound is a terbium cryptate and wherein the fluorescent acceptor compound is selected from rhodamine, thionine, R phycocyanine, phycoerythrocyanine, C phycoerythrin, B phycoerythrin or R phycoerythrin.

10. The method according to claim 1 including the additional step of incubating said medium after each addition of reagents or after the addition of the two reagents, prior to exciting the resulting mixture.

11. The method according to claim 10 wherein said first reagent includes at least one receptor for said analyte, said first reagent having a receptor coupled with a luminescent donor compound consisting of a europium or terbium chelate or cryptate, and wherein said second reagent consists of one or more different receptors for said analyte, said second reagent being coupled with a luminescent acceptor compound.

12. The method according to claim 10 wherein said first reagent includes a receptor for said analyte, coupled with a luminescent donor compound consisting of a europium or terbium chelate or cryptate, and wherein said second reagent includes the analyte coupled with a luminescent acceptor compound.

13. The method according to claim 10 wherein said first reagent includes a receptor for said analyte, said receptor being coupled with a luminescent acceptor compound, and wherein said second reagent includes the analyte coupled with a luminescent donor compound.

14. A homogenous luminescent method of detecting and/or determining an analyte in a medium in which it may be present, said method comprising the steps of:

1) adding to said medium a first reagent consisting of at least one receptor which specifically binds to said analyte, 2) adding a second reagent selected from the analyte or at least one receptor which specifically binds to the analyte, 3) selecting and coupling a luminescent donor compound to one of the two reagents, said luminescent donor compound consisting of a europium cryptate, and said luminescent donor compound having a low overall quantum yield, 4) selecting and coupling a luminescent acceptor compound to the other reagent, said luminescent acceptor compound selected from the group consisting of allophycocyanine, allophycocyanine B, C phycocyanine, and R phycocyanine, and said luminescent acceptor compound having a quantum yield greater than the yield of radiative deactivation of the emission level of the europium ion of said luminescent donor compound, 5) exciting the mixture with a light source at the excitation wavelength of said luminescent donor compound such that the transfer efficiency between said luminescent donor compound and said luminescent acceptor compound times the quantum yield of said luminescent acceptor compound is greater than the quantum yield of radiative deactivation of the emission level of the europium ion of said luminescent donor compound, to amplify the emission signal of said luminescent donor compound, 6) measuring the emission signal of the luminescent acceptor compound, and 7) correlating the measured emission signal of the luminescent acceptor compound to the presence and/or amount of analyte.

15. A homogenous luminescent method of detecting and/or determining an analyte in a medium in which it may be present, said method comprising the steps of:

1) adding to said medium a first reagent consisting of at least one receptor which specifically binds said analyte, 2) adding a second reagent selected from the analyte or at least one receptor which specifically binds to the analyte, 3) selecting and coupling a luminescent donor compound to one of the two reagents, said luminescent donor compound consisting of a terbium cryptate, and said luminescent donor compound having a low overall quantum yield, 4) selecting and coupling a luminescent acceptor compound to the other reagent, said luminescent acceptor compound selected from the group consisting of rhodamine, thionine, R phycocyanine, phycoerythrocyanine, C phycoerythrin, B phycoerythrin, and R phycoerythrin, and said luminescent acceptor compound having a quantum yield greater than the yield of radiative deactivation of the emission level of the terbium ion of said luminescent donor compound, 5) exciting the mixture with a light source at the excitation wavelength of said luminescent donor compound such that the transfer efficiency between said luminescent donor compound and said luminescent acceptor compound times the quantum yield of said luminescent acceptor compound is greater than the quantum yield of radiative deactivation of the emission level of the terbium ion of said luminescent donor compound, to amplify the emission signal of said luminescent donor compound, 6) measuring the emission signal of the luminescent acceptor compound, and 7) correlating the measured emission signal of the luminescent acceptor compound to the presence and/or amount of analyte.

* * * * *